(12) United States Patent
Babikyan et al.

(10) Patent No.: US 10,858,308 B2
(45) Date of Patent: Dec. 8, 2020

(54) COMPOUNDS AND COMPOSITIONS

(71) Applicant: Alectrona PTE. LTD., Singapore (SG)

(72) Inventors: Gaik Babikyan, Jakarta (ID);
Benjamin Jiaravanon, Singapore (SG)

(73) Assignee: Alectrona PTE. LTD., Singapore (SG)

( * ) Notice: Subject to any disclaimer, the term of this patent is extended or adjusted under 35 U.S.C. 154(b) by 0 days.

(21) Appl. No.: 16/476,977

(22) PCT Filed: Jan. 10, 2018

(86) PCT No.: PCT/SG2018/050012
§ 371 (c)(1),
(2) Date: Jul. 10, 2019

(87) PCT Pub. No.: WO2018/132066
PCT Pub. Date: Jul. 19, 2018

(65) Prior Publication Data
US 2019/0352253 A1    Nov. 21, 2019

(30) Foreign Application Priority Data
Jan. 10, 2017   (GB) .................................. 1700404.5

(51) Int. Cl.
| | | |
|---|---|---|
| *C07C 227/08* | (2006.01) | |
| *C07C 227/40* | (2006.01) | |
| *A61P 31/10* | (2006.01) | |
| *A61P 31/20* | (2006.01) | |
| *A61P 31/22* | (2006.01) | |
| *A61P 31/04* | (2006.01) | |
| *C07C 229/16* | (2006.01) | |

(52) U.S. Cl.
CPC ............ *C07C 229/16* (2013.01); *A61P 31/04* (2018.01); *A61P 31/10* (2018.01); *A61P 31/20* (2018.01); *A61P 31/22* (2018.01); *C07C 227/08* (2013.01); *C07C 227/40* (2013.01)

(58) Field of Classification Search
CPC ..... C07C 227/08; C07C 227/40; A61P 31/10; A61P 31/20; A61P 31/22; A61P 31/04
See application file for complete search history.

(56) References Cited

FOREIGN PATENT DOCUMENTS

| | | |
|---|---|---|
| CN | 1683317 A | 10/2005 |
| GB | 1258924 A | 12/1971 |
| JP | 2005162769 A | 6/2005 |
| WO | 2004020729 A1 | 3/2004 |

OTHER PUBLICATIONS

Carbone-Howell et al., 2014, caplus an 2014:560756.*
Chayavichitsilp P, Buckwalter JV, Krakowski AC, Friedlander SF (Apr. 2009). "Herpes simplex". Pediatr Rev. 30 (4).
Combined Search and Examination Report in Application No. GB1700404.5, dated Oct. 31, 2017, 6 pgs.
International Search Report and Written Opinion in International Patent Application No. PCT/SG2018/050012, dated Mar. 19, 2018, 9 pgs.
Ljubojevic, Suzana; Skerlev, Mihael (2014). "HPV-associated diseases". Clinics in Dermatology. 32 (2): 227-234.
Milner, Danny A. (2015). Diagnostic Pathology: Infectious Diseases. Elsevier Health Sciences. p. 40.

* cited by examiner

*Primary Examiner* — Sun Jae Yoo
(74) *Attorney, Agent, or Firm* — Wood Herron & Evans LLP

(57) ABSTRACT

Disclosed are compounds having the following formula: (I) wherein R is an alkane chain having between 8 and 20 carbon atoms, and A is one or more anions having a total charge of −2; or R is a quaternary amine having the following formula: (Ia) wherein Ra and Rb are each an alkane chain having between 8 and 20 carbon atoms, and A is one or more anions having a total charge of −3.

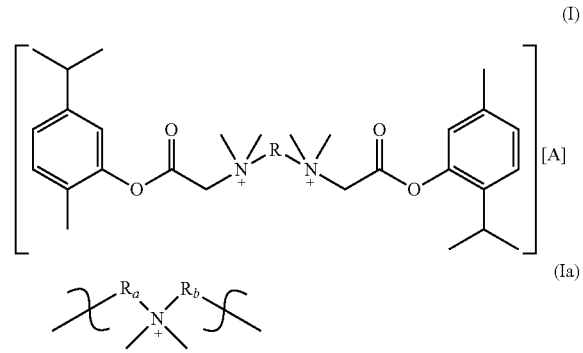

18 Claims, 6 Drawing Sheets

BSC 40 + VV

| 0 | Compound 2 50μg/m | Compound 3 50μg/m |

Figure 7

COMPOUNDS AND COMPOSITIONS

BACKGROUND

The Herpesviridae is a large family of DNA viruses that are responsible for a number of diseases in both humans and animals. The most common Herpesviradae that cause diseases amongst humans are Varicella Zoster virus, Epstein-Barr virus, Cytomegalovirus, Herpes Simplex virus 1 and Herpes Simplex virus 2.

Varicella zoster virus is a common virus that causes chickenpox in children and herpes zoster (shingles) in adults.

Epstein-Barr virus is the virus that commonly causes infectious mononucleosis (glandular fever), while also being associated with cancers such as Hodgkin's lymphoma, Burkitt's Lymphoma and gastric cancer.

Cytomegalovirus, is further member of the Herpesviridae viral family. Human cytomegalovirus (HCMV, or CMV or human herpersvirus-5 (HHV-5)) is a virus associated with the salivary glands and is typically unnoticed by healthy individuals, but can be life threatening for immunocompromised, such as patients having HIV, recipients of organ transplants and new born infants.

Herpes Simplex Virus 1 and Herpes Simplex Virus 2 are both viruses responsible for the viral disease Herpes Simplex. Both viruses can cause oral infections and genital infections, although HSV-1 is more commonly associated with oral infections (e.g. oral herpes), while HSV-2 is more commonly associated with genital infections (e.g. genital herpes). The Herpes Simplex viruses cause infections that affect between approximately 60% and 95% of adults world wide (Chayavichitsilp P, Buckwalter J V, Krakowski A C, Friedlander S F (April 2009). "*Herpes simplex*". *Pediatr Rev.* 30 (4)).

Oral herpes is typically associated with the face and/or the mouth and may result in small blisters that form Herpes labialis (cold sores). Oral Herpes can also include other symptoms such as sore throat, fever, muscle pains, swollen lymph nodes, head ache and malaise, particularly in the first episode after the patient becomes infected.

Genital herpes is typically associated with the genitals and may result in small lesions in the genital regions, inner thigh, buttocks and/or anus. Other typical symptoms associated with this virus include pain, itching, burning, discharge, fever, headache, muscle pain, swollen lymph nodes and malaise.

Oral Herpes may be treated with antiviral drugs, which can reduce the duration of the symptoms, but not completely kill the responsible virus. After the symptoms of an oral herpes infection resolve, the herpes virus (e.g. HSV-1 or HSV-2) generally remains dormant in the facial nerve branches, and the virus may periodically reactivate to create Herpes labialis in the same area of the mouth or face as the site of the original infection. In some humans, the virus remains asymptomatic, although transmission may be possible even when symptoms are not present.

Genital herpes can also be treated with antiviral drugs, which may reduce the duration of the symptoms. However, as for oral herpes, there is no licensed medication that completely eradicates the responsible virus from the human body.

Human Papilloma virus (HPV) is responsible for Human papillomavirus infection which generally cause no symptoms and resolve spontaneously. However, in some cases infections persist and result in warts or precancerous lesions. The precancerous lesions may increase the risk of a number of cancer types, and these include cancer of the cervix, vagina, penis, anus, mouth and throat (Ljubojevic, Suzana; Skerlev, Mihael (2014). "*HPV-associated diseases*". Clinics in Dermatology. 32 (2): 227-234). HPV is the most common sexually transmitted infection globally and most people are infected at some point during their lives (Milner, Danny A. (2015). *Diagnostic Pathology: Infectious Diseases*. Elsevier Health Sciences. p. 40).

Bacterial and fungal infections are common throughout the world. Various drugs have been developed to treat such infections and these may target specific or broad types of bacterial and fungal species and strains. Antibiotic resistance, and more recently antifungal resistance, is becoming more prevalent and an ever increasing problem world wide. With this in mind, there is a global need for new drugs that are able to treat bacterial and fungal infections.

Bearing in mind the prevalence of the Herpes virus (particularly Herpes Simplex virus) and Human papilloma virus, as well as the range of diseases associated with these viruses, there is a need for a treatment that targets these viruses and can treat the diseases associated with these viruses.

In a first aspect of the present invention there is provided a compound having the following formula:

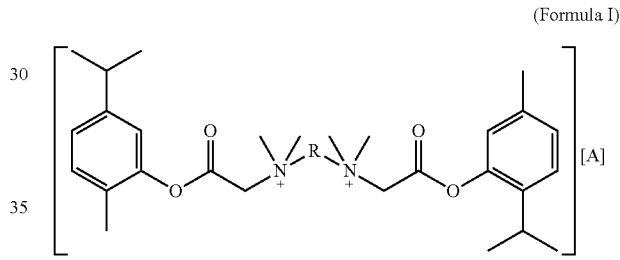

(Formula I)

wherein, R is an alkane chain having between 8 and 20 carbon atoms and A is one or more anions having a total charge of −2; or R is a quaternary amine having the following formula:

(Ia)

wherein $R_a$ and $R_b$ are each an alkane chain having between 8 and 20 carbon atoms, and A is one or more anions having a total charge of −3.

R may be, for example, a linear or branched saturated alkane chain having between 8 and 18 carbon atoms, for example 8 and 16 carbon atoms, for example 8 and 14 carbon atoms, for example 9 and 15 carbon atoms, for example 10 carbon atoms. Preferably, R is a linear saturated alkane chain having between 8 and 16 carbons, for example 10 carbon atoms.

R may be, for example, a quaternary amine according to formula (Ia), in which $R_a$ and $R_b$ are each linear or branched saturated alkane chains having between 8 and 18 carbon atoms, for example 8 and 16 carbon atoms, for example 8 and 14 carbon atoms, for example 9 and 15 carbon atoms, for example 10 carbon atoms. $R_a$ and $R_b$ may each be linear or branched saturated alkane chains having a different number of carbon atoms.

Preferably, $R_a$ and $R_b$ are each linear saturated alkane chains having between 8 and 16 carbon atoms, for example 10 carbon atoms.

A saturated linear alkane chain may be represented by the following formula:

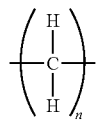

wherein n is the number of repeat units, that is the number of carbon atoms in the linear alkane chain. Thus, in the case of R being an alkane chain having between 8 and 20 carbon atoms, it is preferred that R is

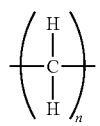

wherein n is between 8 and 16, for example 10. In the case of R being a quaternary amine having the formula (Ia) as set out above, it is preferred that $R_a$ and $R_b$ is

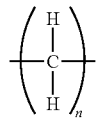

wherein n is between 8 and 16, for example 10.

A may, for example, comprise halide ions, such as chloride (Cl$^-$) ions, bromide (Br$^-$) ions, iodide ions (I$^-$) and/or fluoride ions (F$^-$). A may, for example, comprise ions of other organic and non-organic acids, such as sulphate (SO$_4^{2-}$), carbonate (CO$_3^{2-}$), hydrogen carbonate (HCO$_3^-$), hydrogen sulphate (HSO$_4^-$), acetate ions (CH$_3$COO$^-$), and/or formate ions (HCOO$^-$). In the case of R being an alkane chain having between 8 and 20 carbon atoms, preferably A comprises two halide ions, for example two chloride ions, thus having a total charge of −2. In the case of R being a quaternary amine having formula (Ia) as set out above, preferably A comprises two chloride ions and a bromide ion, thus having a total charge of −3.

Preferably, the compound of formula I above has the following formula:

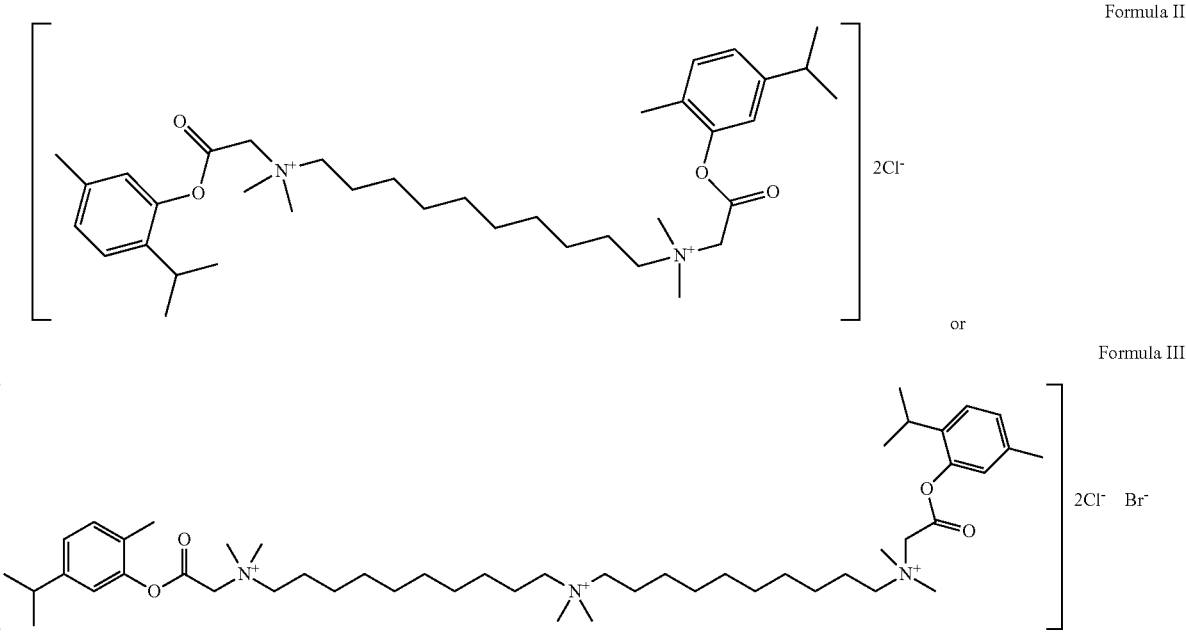

Formula II or

Formula III

Referring to formula II, R is a linear saturated alkane chain having 10 carbon atoms; and A is two chloride ions. Referring to formula III, R is a quaternary amine, in which $R_a$ and $R_b$ are each saturated linear alkane chains having 10 carbon atoms, and A is two chloride ions and one bromide ion.

In another embodiment of the invention, there is provided a compound having the following formula:

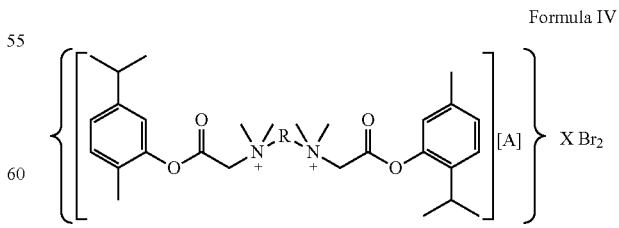

Formula IV wherein R is an alkane chain having between 8 and 20 carbon atoms, and A is one or more anions having a total charge of −2; or R is a quaternary amine having the following formula:

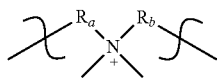
(Ia)

wherein $R_a$ and $R_b$ are each an alkane chain having between 8 and 20 carbon atoms, and A is one or more anions having a total charge of −3; and wherein X is 2, 4, 6, 8 or 10.

R may be, for example, a linear or branched saturated alkane chain having between 8 and 18 carbon atoms, for example 8 and 16 carbon atoms, for example 8 and 14 carbon atoms, for example 9 and 15 carbon atoms, for example 10 carbon atoms. Preferably, R is a linear saturated alkane chain having between 8 and 16 carbons, for examples 10 carbon atoms.

R may be, for example, a quaternary amine according to formula (Ia), in which R and $R_b$ are each linear or branched saturated alkane chains having between 8 and 18 carbon atoms, for example 8 and 16 carbon atoms, for example 8 and 14 carbon atoms, for example 9 and 15 carbon atoms, for example 10 carbon atoms. $R_a$ and $R_b$ may each be linear or branched saturated alkane chains having a different number of carbon atoms.

Preferably, $R_a$ and $R_b$ are each linear saturated alkane chains having between 8 and 16 carbon atoms, for example 10 carbon atoms.

A saturated linear alkane chain may be represented by the following formula:

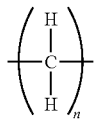

wherein n is the number of repeat units, that is the number of carbon atoms in the linear alkane chain. Thus, in the case of R being an alkane chain having between 8 and 20 carbon atoms, it is preferred that R is

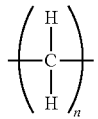

wherein n is between 8 and 16, for example 10. In the case of R being a quaternary amine having the formula (Ia) as set out above, it is preferred that $R_a$ and $R_b$ is

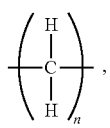

wherein n is between 8 and 16, for example 10.

A may, for example, comprise halide ions, such as chloride ($Cl^-$) ions, bromide ($Br^-$) ions iodide ions ($I^-$) and/or fluoride ions ($F^-$). A may, for example comprise ions of other organic and non-organic acids, such as sulphate ($SO_4^{2-}$), carbonate ($CO_3^{2-}$), hydrogen carbonate ($HCO_3^-$), hydrogen sulphate ($HSO_4^-$), acetate ($CH_3COO^-$), and/or formate ions ($HCOO^-$). In the case of R being an alkane chain having between 8 and 20 carbon atoms, preferably A comprises two halide ions, for example two chloride ions, thus having a total charge of −2. In the case of R being a quaternary amine having formula (Ia) as set out above, preferably A comprises two chloride ions and a bromide ion, thus having a total charge of −3.

Preferably, the compound of formula IV above has the following formula:

Formula V

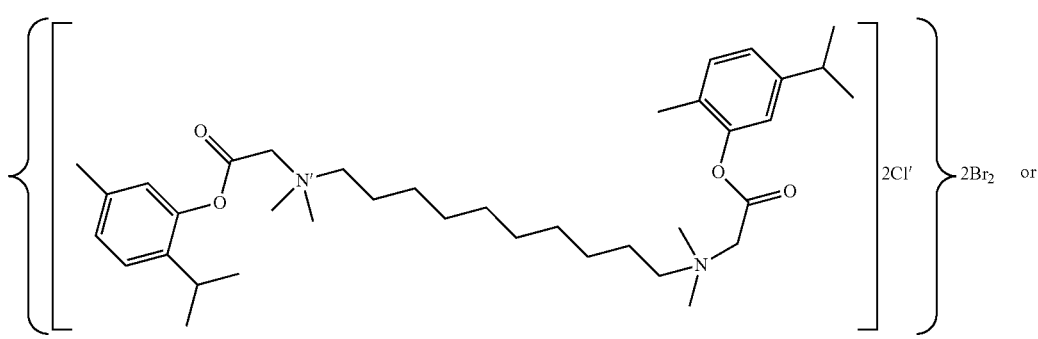

formula (VI)

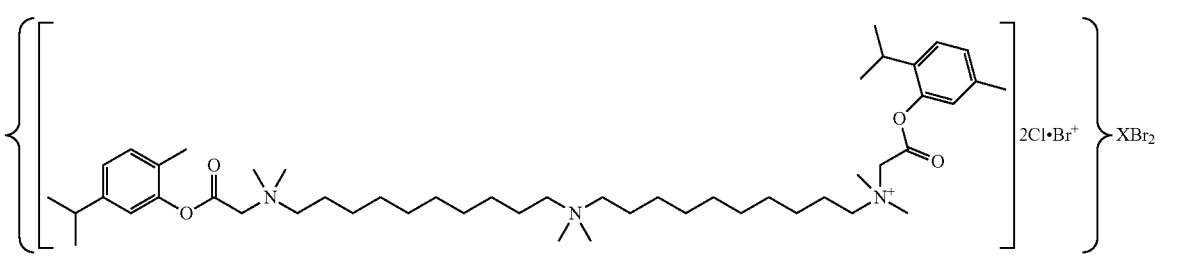

wherein X is 4, 8 or 10.

Referring to formula V, R is a linear saturated alkane chain having 10 carbon atoms; and A is two chloride ions.

Referring to formula VI, R is a quaternary amine, in which $R_a$ and $R_b$ are each saturated linear alkane chains having 10 carbon atoms, and A is two chloride ions and one bromide ion.

The applicant has found that the above compounds represented by formula I-VI demonstrate surprising anti bacterial and antifungal activity. Without being bound by any particular theory, it is hypothesised that this antibacterial and antifungal activity may stem from the combination of the aromatic thymol and carvacrol groups, quaternary ammonia groups and long chain alkyl groups. Additionally, complexing compounds according to formulae I-III with bromine may further increase their antibacterial and antifungal properties.

Additionally, based on computer modelling, the applicant has found that compounds according to the formulas I-VI, which include a combination of the thymol, carvacrol, quaternary ammonia and long chain alkane groups may have antiviral activity, being effective against, for example, the Herpes viruses, for example Herpes Simplex viruses and Human Papilloma Virus.

Without being bound to any particular theory, it is predicted that the compounds of formula I-VI should be able to possess direct antiviral activity against viral particles prior to virus-target cell interaction due to chemical interaction with the main biological macromolecules such as proteins, lipids and nucleoproteins. The compounds of formula I-VI should be able to disrupt the early stage of virus and target cell interaction including virus adherence, cellular receptor interaction and virus entry into the cell. Compounds according to formulae I-VI should be potent as apoptotic cell death inducing agents during interaction with the cells intracellular infected by viruses.

In another aspect of the invention, there is provided a pharmaceutical composition (for example a human pharmaceutical composition and/or a veterinary pharmaceutical composition), comprising a compound according to formulae I to VI above.

The pharmaceutical composition may be in a form suitable for one or more of oral, rectal, parenteral, transdermal, intravenous, intra-arterial, intraosseous infusion, intracerebral, intracerebroventricular, intrathecal, intramuscular, subcutaneous, intravaginal, intraperitoneal, epidural, intracerebral, intraosseous infusion, intravitreal, transmucosal, buccal, or nasal administration.

The pharmaceutical composition may comprise a compound according to formulae I to VI, a pharmaceutically acceptable carrier, such as aqueous solution, non toxic excipients, including salts and preservatives, buffers and the like.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

Examples of pharmaceutically acceptable excipients include antiadherents, binders, coatings, colourings, disintegrant, flavourings, glidants, lubricants, preservatives, sorbents and sweeteners.

The pharmaceutical compositions of the present invention may also contain additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, and the like.

A pharmaceutical composition suitable for oral administration may be in the form of, for example, a tablet, a pill, a sugar coated agent, a powder, a capsule, a liquid, a gel, a syrup, a slurry, a suspension, a cachet and the like. The composition may comprise a pharmaceutically acceptable carrier, for example liposomes, lactose, trehalose, sucrose, mannitol, xylitol, crystalline cellulose, chitosan, calcium carbonate, talc, titanium oxide, silica and the like.

The pharmaceutical composition may be obtained, for example, by combining the compounds of the invention with a solid excipient, pulverizing the mixture (if necessary) and inserting into a capsule, for example, a soft sealed capsule consisting of a gelatin capsule, gelatin and coating (e.g., glycerol or sorbitol) or a capsule composition suitable for vegetarians. In the soft capsule, the composition may be dissolved or suspended in an appropriate liquid, such as a fatty oil, liquid paraffin or liquid polyethylene glycol, with or without a stabilizer.

In a further aspect of the present invention there is provided a compound or a pharmaceutical composition as set out above for use as a medicament.

In a further aspect of the present invention there is provided a compound or a pharmaceutical composition as set out above for use in the treatment of Herpes virus, Human Papilloma Virus, bacterial infections and/or fungal infections.

The Herpes virus may be one or more of a Herpes Simplex virus, Herpes Simplex virus 1 (HSV-1), Herpes Simplex virus 2 (HSV-2), Varicella zoster virus (VZV), Epstein-Barr virus, Cytomegalovirus, Roseolovirus, Kaposi's Sarcoma-associated herpesvirus, animal Herpesviruses, such as Pseudorabies virus, and Bovine herpesvirus 1.

Preferably, the Herpes virus is a Herpes Simplex virus (for example Herpes Simplex virus 1 or Herpes Simplex virus 2) or Cytomegalovirus.

The bacterial infections may include those caused by gram positive and/or gram negative bacteria.

The bacterial infections may be caused by, for example, *Staphylococcus aureus* and/or *Salmonella enterica* bacteria.

The fungal infections may be superficial mycoses, cutaneous mycoses, subcutaneous mycoses, and/or systemic mycoses.

The fungal infections may be caused by, for example, *Candida albicans.*

In a further aspect of the invention, there is provided the use of a compound or pharmaceutical composition as set out above in the manufacture of a medicament for treating Herpes virus, Human Papilloma Virus, bacterial infections and/or fungal infections.

The herpes virus may be one or more of a Herpes Simplex virus, Herpes Simplex virus 1 (HSV-1), Herpes Simplex virus 2 (HSV-2), Varicella zoster virus (VZV), Epstein-Barr virus, Cytomegalovirus, Roseolovirus, Kaposi's Sarcoma-associated herpesvirus, animal Herpesviruses, such as Pseudorabies virus, and Bovine Herpesvirus 1.

Preferably, the Herpes virus is a Herpes Simplex virus (for example Herpes Simplex virus 1 or Herpes Simplex virus 2) or Cytomegalovirus.

The bacterial infections may include those caused by gram positive and/or gram negative bacteria.

The bacterial infections may be caused by, for example, *Staphylococcus aureus* and/or *Salmonella enterica* bacteria.

The fungal infections may be superficial mycoses, cutaneous mycoses, subcutaneous mycoses, and/or systemic mycoses.

The fungal infections may be caused by, for example, *Candida albicans*.

In a further aspect of the invention, there is provided a method of treatment of Herpes virus, Human Papilloma Virus, bacterial infections and/or fungal infections, comprising a step of administering to a subject a compound or pharmaceutical composition as set out above.

The herpes virus may be one or more of a Herpes Simplex virus, Herpes Simplex virus 1 (HSV-1), Herpes Simplex virus 2 (HSV-2), Varicella zoster virus (VZV), Epstein-Barr virus, Cytomegalovirus, Roseolovirus, Kaposi's Sarcoma-associated Herpesvirus, animal Herpesviruses, such as Pseudorabies virus, and Bovine Herpesvirus 1.

Preferably, the herpes virus is a Herpes Simplex virus (for example Herpes Simplex virus 1 or Herpes Simplex virus 2) or Cytomegalovirus.

The bacterial infections may include those caused by gram positive and/or gram negative bacteria.

The bacterial infections may be caused by, for example, *Staphylococcus aureus* and/or *Salmonella enterica* bacteria.

The fungal infections may be superficial mycoses, cutaneous mycoses, subcutaneous mycoses, and/or systemic mycoses.

The fungal infections may be caused by, for example, *Candida albicans*.

In a further aspect of the invention there is provided a process for the production of the compounds set out above in formulae I-III comprising the following steps:
i) reacting carvacrol with $R_2CH_2COCl$ to form a compound having the formula:
wherein $R_2$ is a halogen, for example chlorine or bromine;

(formula VII)

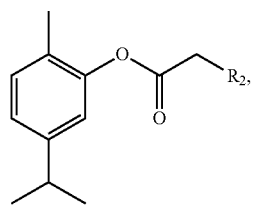

ii) reacting the compound having the formula (formula VIII)

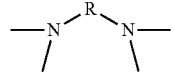

with the compound having the formula (formula VII)

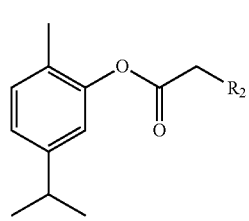

to form the compound having the formula (formula IX)

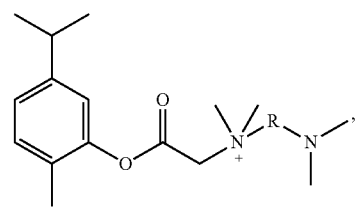

wherein R is an alkane chain having between 8 and 20 carbon atoms; or R is a quaternary amine having the following formula:

(Ia)

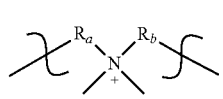

wherein $R_a$ and $R_b$ are each an alkane chain having between 8 and 20 carbon atoms;

iii) reacting thymol with $R_2CH_2COCl$ to form a compound having the formula (formula X)

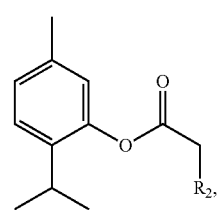

wherein $R_2$ is a halogen, for example chlorine or bromine;

v) reacting the compound having the formula (formula IX)

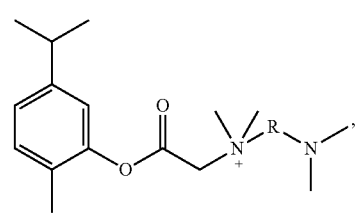

with the compound having the formula (formula X)

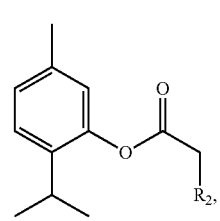

to form the final product having the formula

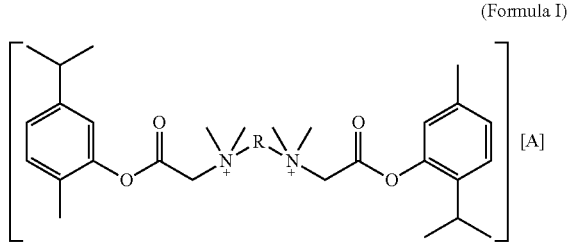

(Formula I)

wherein R is an alkane chain having between 8 and 20 carbon atoms; and A is one or more anions having a total charge of −2; or R is a quaternary amine having the following formula:

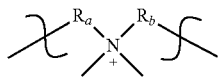

(Ia)

wherein $R_a$ and $R_b$ are each an alkane chain having between 8 and 20 carbon atoms, and A is one or more anions having a total charge of −3.

R may be, for example, a linear or branched saturated alkane chain having between 8 and 18 carbon atoms, for example 8 and 16 carbon atoms, for example 8 and 14 carbon atoms, for example 9 and 15 carbon atoms, for example 10 carbon atoms. Preferably, R is a saturated linear alkane chain having between 8 and 16 carbon atoms, for example 10 carbon atoms.

R may be, for example, a quaternary amine according to formula (Ia), in which $R_a$ and $R_b$ are linear or branched saturated alkane chains having between 8 and 18 carbon atoms, for example 8 and 16 carbon atoms, for example 8 and 14 carbon atoms, for example 9 and 15 carbon atoms, for example 10 carbon atoms. $R_a$ and $R_b$ may each be linear or branched saturated alkane chains having a different number of carbon atoms. Preferably, $R_a$ and $R_b$ are each linear saturated alkane chains having between 8 and 16 carbon atoms, for example 10 carbon atoms.

A saturated linear alkane chain may be represented by the following formula:

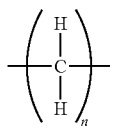

n wherein n is the number of repeat units, that is the number of carbon atoms in the linear alkane chain. Thus, in the case of R being an alkane chain having between 8 and 20 carbon atoms, it is preferred that R is

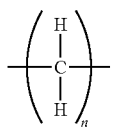

wherein n is between 8 and 16, for example 10. In the case of R being a quaternary amine having the formula (Ia) as set out above, it is preferred that $R_a$ and $R_b$ is

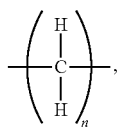

wherein n is between 8 and 16, for example 10.

In the case of R being an alkane chain having between 8 and 20 carbon atoms, the process may include a further step of reacting a compound having the formula

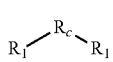

(formula XI)

with four molar equivalents of dimethylamine to form a di tertiary amine having the following formula

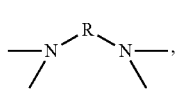

(formula VI)

wherein Rc is an alkane chain having between 8 and 20 carbon atoms, and $R_1$ is a halogen, for example bromine or chlorine; and R is an alkane chain having between 8 and 20 carbon atoms.

In the case of R being a quaternary amine having the following formula:

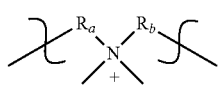

(Ia)

wherein $R_a$ and $R_b$ are each an alkane chain having between 8 and 20 carbon atoms, the process may include a further step of reacting a compound having the formula

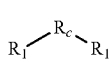

(formula XI)

with three molar equivalents of dimethylamine to form a quaternary amine having the following formula

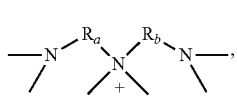

(formula Ib)

wherein Rc is an alkane chain having between 8 and 20 carbon atoms and $R_1$ is a halogen, for example bromine or chlorine; and wherein $R_a$ and $R_b$ are each an alkane chain having between 8 and 20 carbon atoms.

The reactions in steps II and IV may both take place at a temperature of −10° C.

The process may further comprise one or more steps of separation and or extraction, for example a separation step may include column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

In a further aspect of the invention there is provided a process for the production of a compound having formulae IV-VI as set out above, the process comprising reacting (e.g. complexing) the compound having the formula (Formula I)

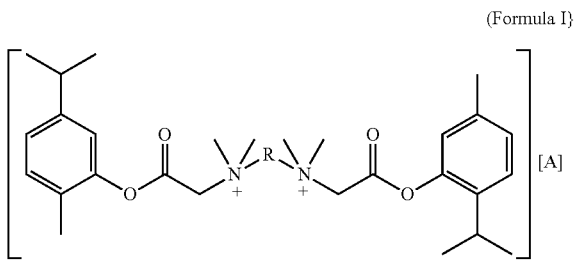

with bromine to form the compound having the formula (formula IV)

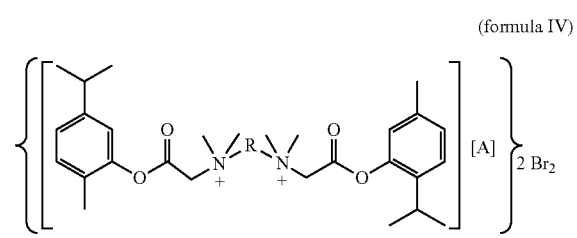

wherein R is an alkane chain having between 8 and 20 carbon atoms, and A is one or more anions having a total charge of −2; or R is a quaternary amine having the following formula:

(Ia)

wherein $R_a$ and $R_b$ are each an alkane chain having between 8 and 20 carbon atoms, and A is one or more anions having a total charge of −3.

In a further aspect of the invention there is provided a process for the production of a compound substantially as described herein with reference to FIG. 1, FIG. 2 or FIG. 3.

In a further aspect of the invention there is provided a compound having the following formula:

(formula I)

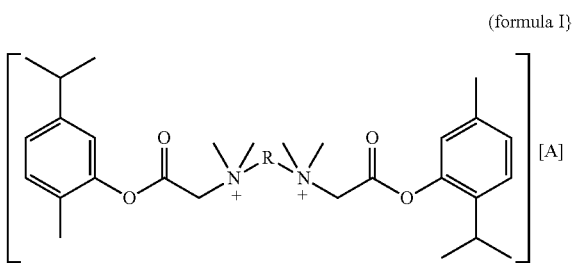

wherein R is an alkane chain having between 8 and 20 carbon atoms; and A is one or more anions having a total charge of −2; or R is a quaternary amine having the following formula:

(Ia)

wherein $R_a$ and $R_b$ are each an alkane chain having between 8 and 20 carbon atoms, and A is one or more anions having a total charge of −3;
and wherein the compound is optionally complexed with bromine.

The present invention will now be described in more detail with reference to the attached drawings, FIGS. 1 to 7, in which FIG. 1 illustrates an example process for the synthesis of a compound of the invention.

FIG. 7 illustrates the results of the effect of compounds of the invention on Vaccinia Virus plaque formation in BSC 40 cells.

PROCESS FOR PRODUCING THE COMPOUNDS OF THE INVENTION

Compound 2

Figure 1:
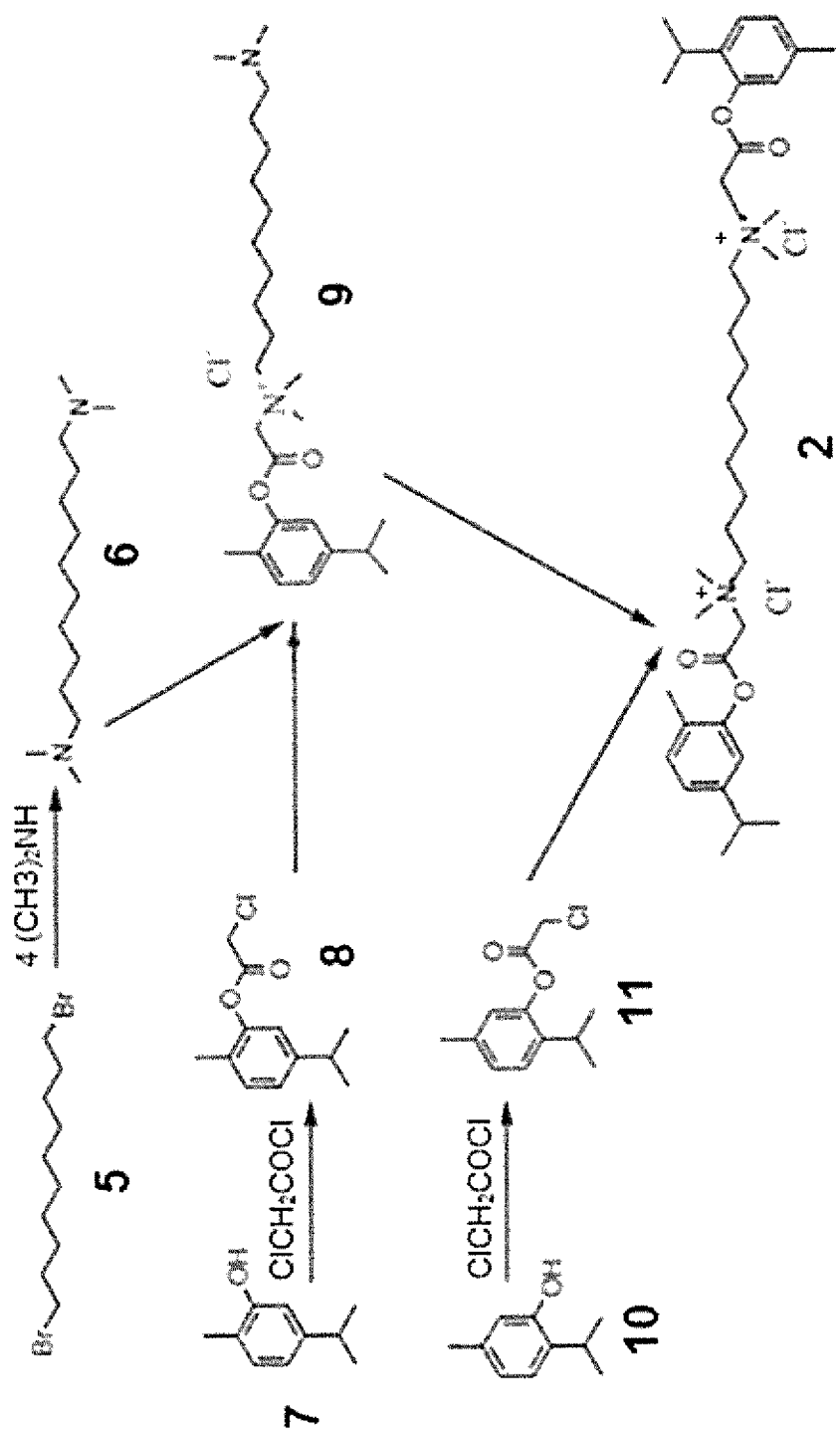

$N^1$-{2-[2-methyl-5-(propan-2-yl)phenoxy]-2-oxo-ethyl}-$N^1$,$N^1$,$N^{10}$,$N^{10}$-tetramethyl-$N^{10}$-{2-[5-methyl-2-(propan-2-yl)phenoxy]-2oxoethyl}decane-1,10-bis(aminium) dichloride FIG. 1 shows an example process for synthesising Compound 2, which is a compound of the invention defined by formula II above.

In a first step, 1,10-Dibromodecane (Compound 5) is reacted with 4 molar equivalents of dimethylamine to form 1,10-Bis(dimethylamino)decane (Compound 6). The reaction takes place at 4-5° C. in benzene and is followed by a step of acid extraction followed by alkaline treatment and extraction with diethyl ether. The extracted fractions are dried over magnesium sulphate and then purified by vacuum distillation.

In a second step, Carvacrol (2-Methyl-5-(1-methylethyl)-phenol) (Compound 7) is reacted with chloroacetyl chloride to form Compound 8. The reaction is carried out at −10° C.

for 1 hour and then stirred at room temperature for 5 hours. The reaction mixture is then washed with acid, followed by treatment with sodium bicarbonate and then water. The organic layer is dried over sodium sulphate, filtered and the solvent is removed under vacuum.

In a third step, Compound 8 is reacted with 1,10-Bis (dimethylamino)decane (Compound 6) to form Compound 9. The reaction is carried out by boiling Compound 6 and Compound 8 in benzene for 15 minutes and then leaving the reaction mixture at room temperature for 24 hours. Ethyl acetate is then added to the reaction mixture, the upper layer is removed and the lower layer is isolated as a residue. The residue (containing Compound 9) is then used in the fifth step.

In a fourth step, thymol (2-isopropyl-5-methylphenol) (Compound 10) is reacted with chloroacetyl chloride to form Compound 11. The reaction is carried out at −10 C for 1 hour and then stirred at room temperature for 5 hours. The reaction mixture is then washed with acid, followed by treatment with sodium bicarbonate and then water. The organic layer is dried over sodium sulphate, filtered and the solvent is removed under vacuum.

In a fifth step, the residue of the third step (containing Compound 9) is reacted with compound 11 to form the final product: Compound 2. The reaction is carried out by boiling Compounds 9 and 11 in benzene for 15 minutes and then leaving the reaction mixture at room temperature for 24 hours. Ethyl acetate is then added to the reaction mixture and the upper layer is removed and the lower layer is isolated as a residue.

The resulting residue is then dissolved in acetone and Compound 2 is precipitated by the addition of diethyl ether.

It will be appreciated that further purification and separation steps may also be included in the process, for example between each of the above steps and also after the process is complete to purify the final compound (Compound 2).

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

Compound 2 was isolated as a brown hygroscopic powder, having the following properties.

Appearance: brown hygroscopic powder

Molecular formula: $C_{38}H_{62}N_2O_4Cl_2$

Molecular weight: 681.81 gmol$^{-1}$

Melting point: 92-96 C

Aqueous solution pH=6

Solubility: soluble in water, acetone, acetonitrile, dimethyl sulfoxide (DMSO); insoluble in diethyl ether, ethyl acetate and hexane $^1$H NMR (DMSO/CCl$_4$—1/3) δ 1.18 (d, 6H, —CH$_3$), 1.22 (d, 6H, —CH$_3$), 1.37-1.40 (m, 12H, —CH$_2$—), 1.81-1.85 (m, 4H, —CH$_2$—), 2.17 (s, 3H, Ar—CH$_3$), 2.32 (s, 3H, Ar—CH$_3$), 2.87 (q, 1H, —CH), 3.04 (q, 1H, —CH), 3.47 (s, 12H, +N(CH$_3$)$_2$), 3.80-3.85 (m, 4H, +N—CH$_2$—), 5.33 (s, 4H, —(C=O)—CH$_2$—N+), 6.96-7.02 (m, 4H, Ar—H), 7.16-7.20 (m, 2H, Ar—H).

Compound 4

Di-Bromine Complex

Figure 2:
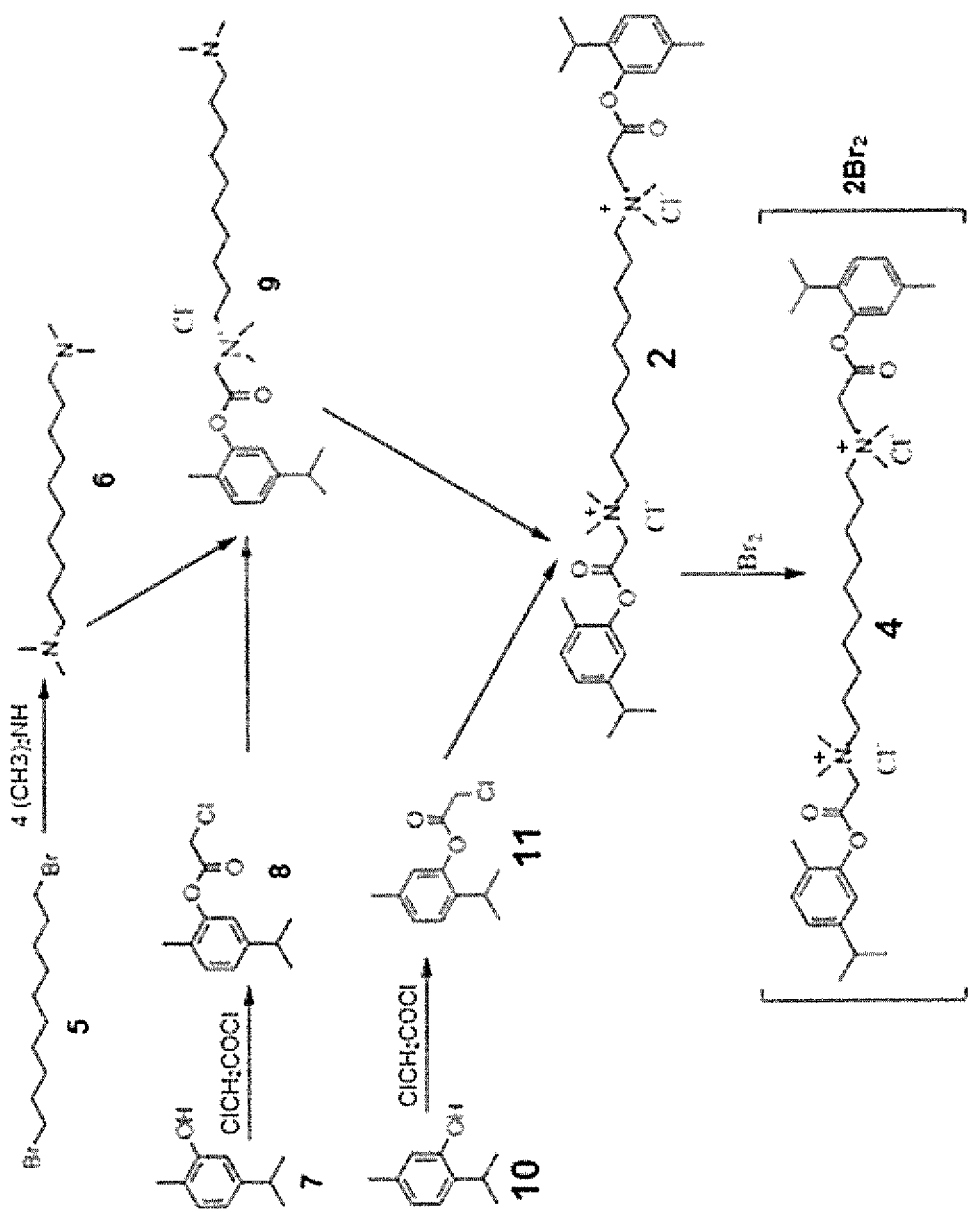
FIG. 2 illustrates an example process for the synthesis of a further compound of the invention.

N$^1$-{2-[2-methyl-5-(propan-2-yl)phenoxy]-2-oxoethyl}-N$^1$,N$^1$,N$^{10}$,N$^{10}$-tetramethyl-N$^{10}$-{2-[5-methyl-2-(propan-2-yl)phenoxy]-2oxoethyl}decane-1,10-bis(aminium) dichloride FIG. 2 shows an example process for synthesising Compound 4, which is a further compound of the invention and is defined by formula V above.

Compound 2 was synthesised according to the process set out above for Compound 2.

After formation of Compound 2, Compound 2 was reacted with bromine to form Compound 4.

As set out above for Compound 2, it will be appreciated that further purification and separation steps may also be included in the process, for example between each of the above steps and also after the process is complete to purify the final compound (Compound 4).

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

Compound 4 was isolated as an orange gum, having the following properties.

Appearance: orange gum

Molecular formula: $C_{38}H_{62}N_2O_4Cl_2Br_4$

Molecular weight: 1001.41 gmol$^{-1}$

Solubility: soluble in dimethyl sulfoxide (DMSO); insoluble in water.

$^1$H NMR (DMSO/CCl$_4$~1/3) δ 1.18-1.22 (m, 12H, —CH$_3$), 1.37-1.40 (m, 12H, —CH$_2$—), 1.81-1.85 (m, 4H, —CH$_2$—), 2.17 (s, 3H, Ar—CH$_3$), 2.32 (s, 3H, Ar—CH$_3$), 2.87 (q, 1H, —CH), 3.04 (q, 1H, —CH), 3.47 (s, 2H, +N(CH$_3$)$_2$), 3.80-3.85 (m, 4H, +N—CH$_2$—), 5.33 (s, 4H, —(C=O)—CH$_2$—N+), 6.96-7.02 (m, 4H, Ar—H), 7.16-7.20 (m, 2H, Ar—H).

Compound 3

Figure 3:
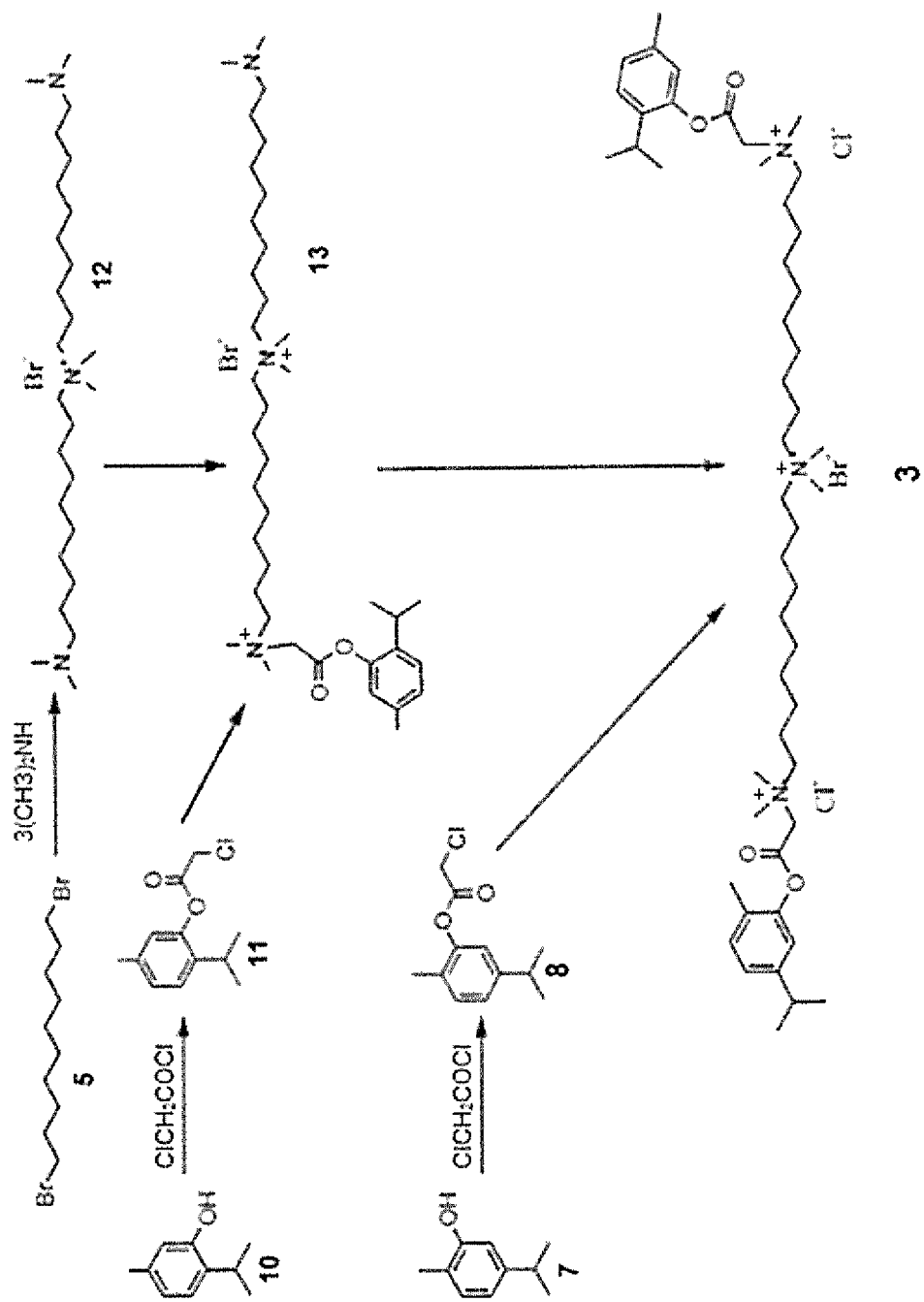
FIG. 3 illustrates an example process for the synthesis of a further compound of the invention.

Systematic Name: N$^1$-{{2-[2-methyl-5-(propan-2-yl)phenoxy]-(2-oxoethyldimethyl)azaniumyl bromide}decyl}-N$^{10}$-{2-[5-methyl-2-(propan-2-yl)phenoxy]-2oxoethyl}-N$^1$,N$^1$,N$^1$,N$^{10}$,N$^{10}$-tetramethyldecane-1,10-bis(aminium) dichloride FIG. 3 shows an example process for synthesising Compound 3, which is a compound of the invention defined by formula III above.

In a first step, 1,10-Dibromodecane 5 is reacted with 3 molar equivalents of dimethylamine to form Compound 12. The reaction takes place at 4-5° C. in benzene and is followed by a step of acid extraction followed by alkaline treatment and extraction with diethyl ether. The extracted fractions are dried over magnesium sulphate and then purified by vacuum distillation.

In a second step, thymol (2-isopropyl-5-methylphenol) (Compound 10) is reacted with chloroacetyl chloride to form Compound 11. The reaction is carried out at −10 C for 1 hour and then stirred at room temperature for 5 hours. The reaction mixture is then washed with acid, followed by treatment with sodium bicarbonate and then water. The organic layer is dried over sodium sulphate, filtered and the solvent is removed under vacuum.

In a third step, Compound 11 is reacted with Compound 12 to form Compound 13. The reaction is carried out by boiling Compounds 11 and 12 in benzene for 15 minutes and then leaving the reaction mixture at room temperature for 24 hours. Ethyl acetate is then added to the reaction mixture and the upper layer is removed and the lower layer is isolated as a residue. The residue (containing Compound 13) is then used in the fifth step.

In a fourth step, Carvacrol (2-Methyl-5-(1-methylethyl)-phenol) (Compound 7) is reacted with chloroacetyl chloride to form Compound 8. The reaction is carried out at −10° C. for 1 hour and then stirred at room temperature for 5 hours. The reaction mixture is then washed with acid, followed by treatment with sodium bicarbonate and then water. The organic layer is dried over sodium sulphate, filtered and the solvent is removed under vacuum.

In a fifth step, the residue of the third step (containing Compound 13) is reacted with Compound 8 to form the final product: Compound 3. The reaction is carried out by boiling Compounds 8 and 13 in benzene for 15 minutes and then leaving the reaction mixture at room temperature for 24 hours. Ethyl acetate is then added to the reaction mixture and the upper layer is removed and the lower layer is isolated as a residue.

The residue is then dissolved in acetone and Compound 3 is precipitated by the addition of diethyl ether.

It will be appreciated that further purification and separation steps may also be included in the process, for example between each of the above steps and also after the process is complete to purify the final compound (Compound 3).

Separation steps may include steps of performing column chromatography, low pressure liquid chromatography, high performance liquid chromatography and the like. Purification steps may include standard purification processes known in the art, for example, filtration, evaporation, liquid-liquid extraction, crystallisation, adsorption, recrystallization, chromatography, distillation and the like.

Compound 3 was isolated as a brown hygroscopic powder, having the following properties.

Appearance: brown hygroscopic powder
Molecular formula: $C_{50}H_{88}N_3O_4 2ClBr$
Molecular weight: 946.06 gmol$^{-1}$
Melting point: 75-78° C.
Aqueous solution pH=7.2
Solubility: soluble in water, acetone, dimethyl sulfoxide (DMSO); insoluble in diethyl ether and ethyl acetate.
Displays Surfactant Activity
$^1$H NMR (DMSO/CCl$_4$—1/3) δ 1.18-1.23 (m, 12H, —CH$_3$), 1.38-1.42 (m, 24H, —CH$_2$—), 1.80-1.84 (m, 8H, —CH$_2$—), 2.18 (s, 3H, Ar—CH$_3$), 2.34 (s, 3H, Ar—CH$_3$), 2.90-3.10 (m, 2H, —CH), 3.45-3.50 (m, 18H, +N(CH$_3$)$_2$), 3.75-3.80 (m, 8H, +N—CH$_2$—), 5.22 (s, 4H, —(C=O)—CH$_2$—N+), 6.96-7.02 (m, 4H, Ar—H), 7.16-7.20 (m, 2H, Ar—H), Example 1

Compounds 2, 3 and 4 were tested for anti bacterial and anti fungal activity.

Minimal inhibitory concentration (MIC) of each compound was tested by broth dilution assay.

Equipment
McFarland standard 0.5
Falcon round-bottom 5 ml tubes
Disposable loops (1 µl and 10 µl)
Graduated pipettes (20 µl-1000 µl)
Disposable Petri dishes Media
Sterile normal saline
TSB (Tryptic Soy Broth)
TSA (Tryptic Soy Agar)

Bacterial and Fungal strains
*Salmonella enterica* serovar *Typhimurium* ATCC 14028
*Staphylococcus aureus* ATCC 6538
*Candida albicans* ATCC 10231

Compounds 2, 3 and 4 were diluted in dimethyl sulfoxide (DMSO) at 10 mg/ml and were future 2-fold diluted for testing in TSB.

Method

Day 1

Standardisation of Inoculum

From a pure o/n culture, material from at least 3-4 colonies was chosen and suspended totally in 4 ml saline in tubes. The suspension was mixed.

The turbidity of inoculum was adjusted to match that of standard by comparing visually with the McFarland 0.5 standard using white paper with black lines as background.

The McFarland 0.5 suspension were diluted as follows for the species tested at this course:

Gr-neg.: 10 µl McFarl. 0.5 into 10 ml broth
Gr-pos.: 50 µl McFarl. 0.5 into 10 ml broth The suspensions were used for inoculation within 15 minutes.

Inoculation and Incubation

The Falcon round-bottom 5 ml tubes were inoculated with 500 µl of the inoculum suspension with 500 µl two-fold dilutions of antimicrobial agent using a graduated pipette Tubes were sealed and incubated at 37° C. for 18-22 hours. This was done to avoid losing growth media and to avoid cross contamination.

McFarland 0.5 is approximately $10^8$ CFU/ml. Standardization of inoculum is essential because the interpretation of the results is based on a certain inoculum.

Each tube contained approximately $5 \times 10^5$-$1 \times 10^6$ CFU/ml after inoculation of bacteria and 55 $5 \times 10^3$-$1 \times 10^4$ CFU/ml of yeast.

Day 2

Purity of the inoculum suspension was checked.

Growth in the 3 positive control tubes was checked.

Minimal inhibitory concentration (MIC) was recorded as the lowest concentration of antimicrobial agent with no visible growth.

Results are set out in the table 1 below.

In summary, all compounds tested demonstrated potent anti fungal activity against *Candida albicans*, as well as anti bacterial activity against *Staphylococcus aureus* and *Salmonella enterica* serovar *Typhimurium*.

TABLE 1

Antimicrobial activity of different samples tested in
indented experiments (n = 4) by broth dilution method

| Cultures | Bacterial/yeast cells count (cfu/ml)# | Sample's MIC (µg/ml)[1] | | |
|---|---|---|---|---|
| | | Compound 2 | Compound 3 | Compound 4 |
| Candida albicans | 6 × 10³ | 62.5-125* | 31.25-62.5 | 31.25-62.5 |
| ATCC 10231 | 3 × 10³ | 62.5-125 | 31.25-62.5 | 31.25-62.5 |
| | 6 × 10³ | 62.5-125 | 31.25-62.5 | 31.25-62.5 |
| | 6.5 × 10³ | 62.5-125 | 31.25-62.5 | 31.25-62.5 |
| Staphylococcus | 2.1 × 10⁶ | 31.25-62.5 | 15.6-31.25 | 15.6-31.25 |
| aureus | 1.2 × 10⁶ | 31.25-62.5 | 15.6-31.25 | 31.25-62.5 |
| ATCC 6538 | 2 × 10⁶ | 31.25-62.5 | 15.6-31.25 | 15.6-31.25 |
| | 1.4 × 10⁶ | 31.25-62.5 | 15.6-31.25 | 15.6-31.25 |
| Salmonella enterica | 5 × 10³ | 62.5-125 | 31.25-62.5 | 31.25-62.5 |
| serovar | | 62.5-125 | 31.25-62.5 | 31.25-62.5 |
| Typhimurium | | 62.5-125 | 31.25-62.5 | 31.25-62.5 |
| ATCC 14028 | | 62.5-125 | 31.25-62.5 | 31.25-62.5 |

Represents bacterial/yeast cells count (CFU/ml) tested in 2 repeats in 4 indented experiments.
*numbers in bold were from seeding for detection of final titer of bacterial/yeast cells. This means that numbers in bold represent the bactericide concentration, whereas non bold numbers are the bacteristatic concentration of compounds in the range of the MIC.
[1]MIC determination by broth dilution using Sensititre. 4th Ed. April 2003 Edited by: Rene S. Hendriksen (DFVF)

Example 2

The antiviral effect and cytotoxicity of the compounds of the invention were investigated by testing compounds 2, 3 and 4 in different mammalian cell lines.
Material and Methods
Cells and Viruses Herpes Simplex virus-1 (HSV 1) and vaccinia virus (W) were both tested, and cell lines used included HeLa, BSC 40 and Vero cells.

HeLa, Vero and BSC 40 cells were cultured in Dulbecco's Modified Eagle Medium (DMEM) supplemented with 10% foetal bovine serum (FBS) and 1% penicillin/streptomycin (Gibco) in a 5% $CO_2$ incubator at 37° C.

The Western Reserve strain of Vaccinia virus (WR-VV) was amplified in BSC40 cells, titrated and stored at –80° C.

Herpes Simplex virus 1 (HSV-1) was amplified in Vero cells, titrated and stored at –80° C.
Compounds and Reagents Compounds 2, 3 and 4 (in powder form) were dissolved in absolute ethanol to obtain stock solutions at a concentration of 0.2 g in 1 ml. Aliquots were stored at –20° C. Prior to the experiments, fresh serial dilution was carried out in serum free growth media (DMEM).
Cytotoxicity The cytotoxic effect of the chemicals was tested on HeLa, BSC40 and Vero cells. Cells were seeded in 12 well plates, such that on the following day the plates had 80% confluence. The compounds 2, 3 and 4 were applied to the cells at varying concentrations. After 30 minutes of pre-treatment, growth media was added to the cells in the presence of the same concentration of compounds 2, 3 and 4. Cells were monitored every day, fixed and stained at 48 hours or 72 hours after treatment, and then photographed. All samples were fixed with 4% formaldehyde in $H_2O$ for 20 minutes at room temperature and subsequently stained with Crystal Violet for 30 minutes at room temperature.
Virus Infections and Plaque Assay Freshly confluent cells were infected with WR-VV and HSV-1 (approximately 200 to 300 PFU per well in a 6-well plate or 12 well plate) at 37° C. for 1 hour. The cells were washed and cultured in growth medium containing 1% agarose, and fixed at 2 days post infection.

Alternatively, cells were pre-treated with serum free Dulbecco's Modified Eagle Media (DMEM) or DMEM containing a different concentration of the compounds prior to infection, and compounds 2 and 3 remained in cultures throughout the experiment until cells were 50 fixed as described above. In some experiments, a liquid plaque assay was performed without agar.
Results
Cytotoxicity of Compounds in Different Mammalian Cell Lines In order to test the antiviral effect of the compounds 2, 3 and 4, an appropriate dilution of the compounds was chosen, such that the compounds were not toxic to the cells and such that cell viability was not affected. A variety of compound concentrations were tested in different mammalian cell lines such as HeLa, BSC40 and Vero cells.

Figure 4:
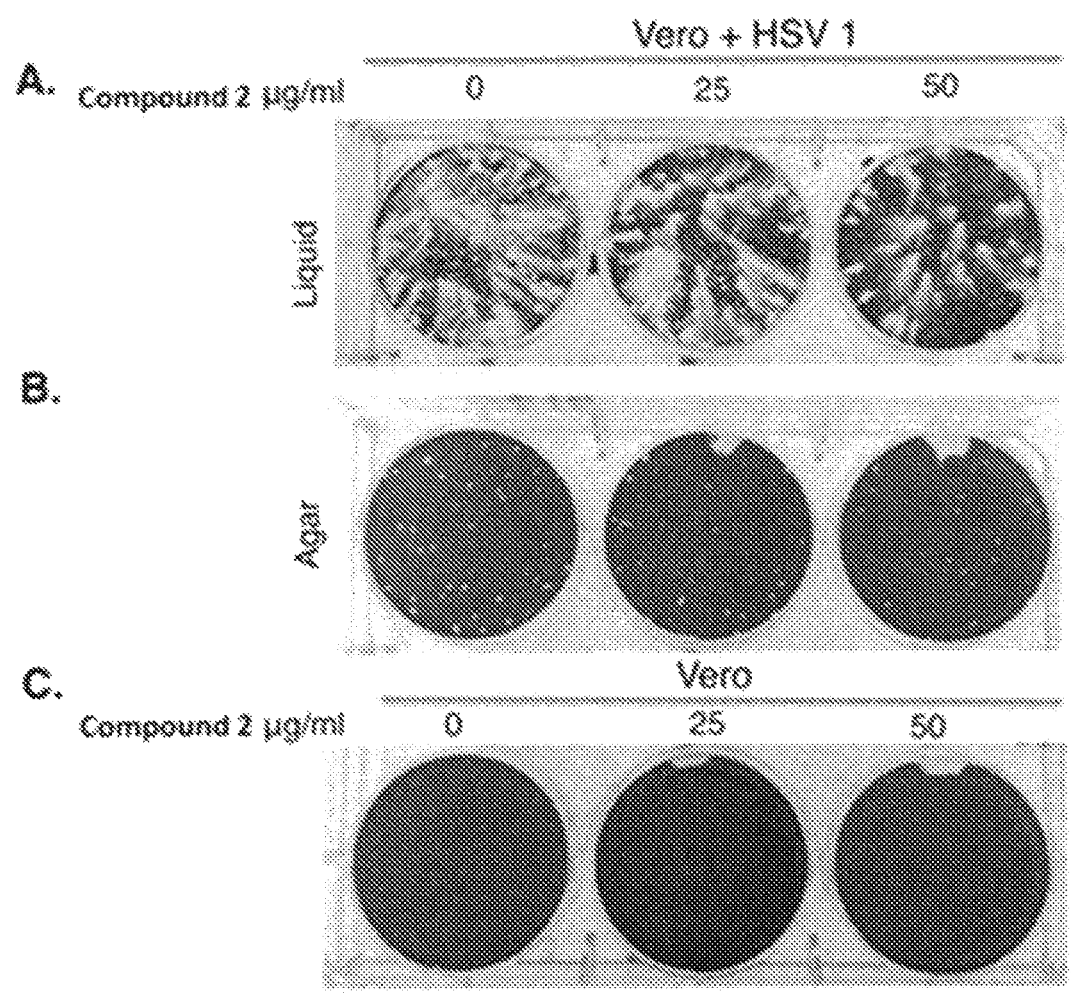
FIG. 4 illustrates the results of cytotoxicity tests of a compound of the invention at concentrations between 0 μg/mL and 50 μg/mL on Vero cells, and the effect of a compound of the invention on Herpes Simplex Virus 1 spread and plaque formation in Vero cells.
Figure 5:
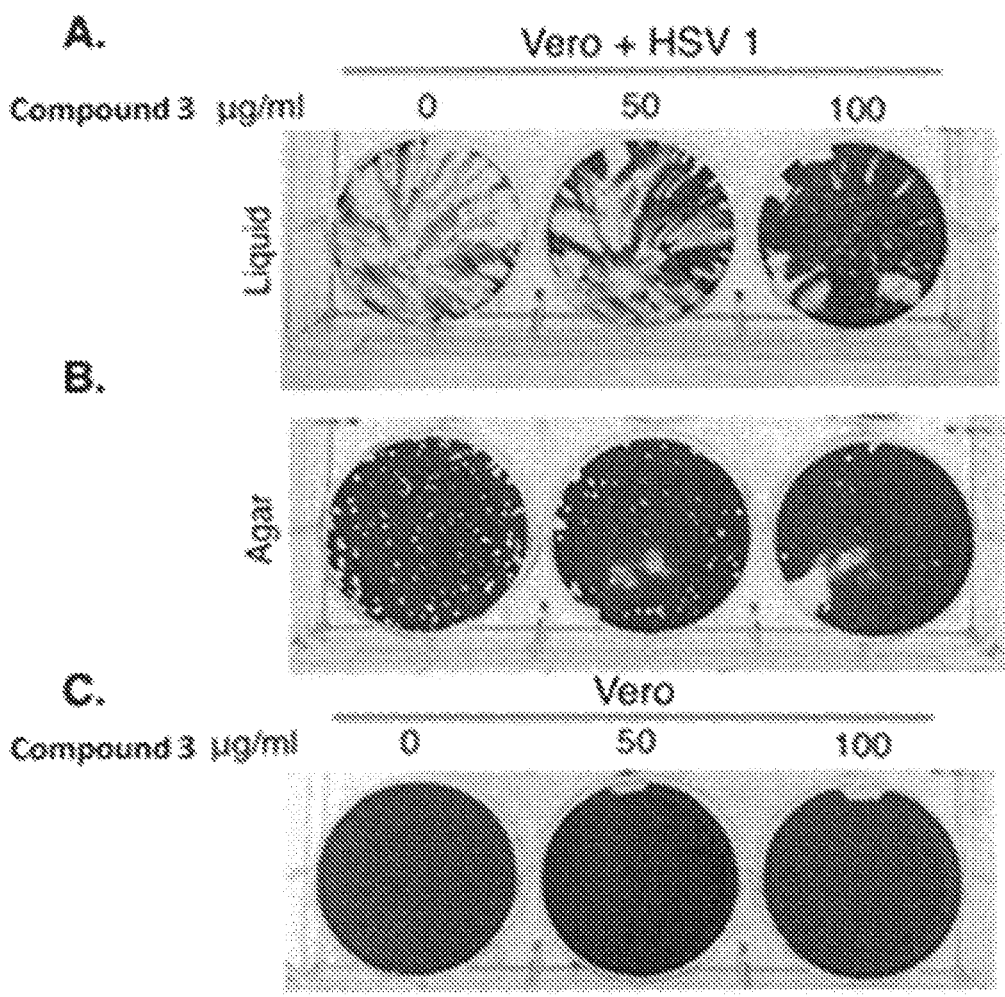
FIG. 5 illustrates the results of cytotoxicity tests of a further compound of the invention at concentrations between 0 μg/mL and 100 μg/mL on Vero cells, and the effect of a further compound of the invention on Herpes Simplex Virus 1 spread and plaque formation in Vero cells.
Figure 6:
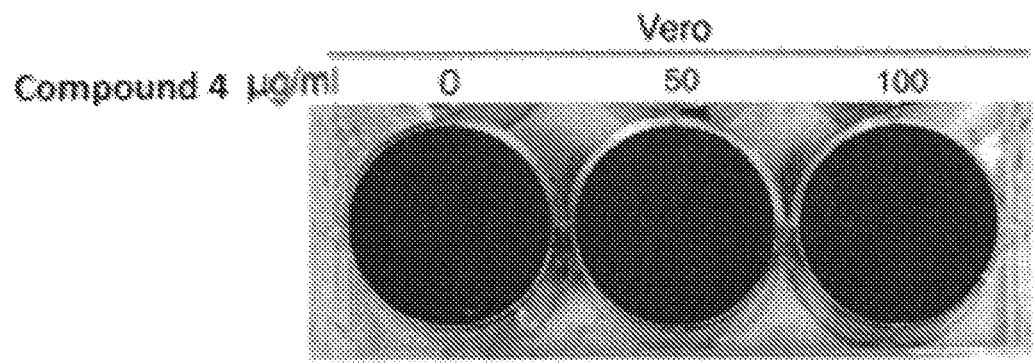
FIG. 6 illustrates the results of cytotoxicity tests of a further compound of the invention at concentrations between 0 μg/mL and 100 μg/mL on Vero cells.

Overnight cultured cells were pre-treated with high to low doses of compounds 2, 3 and 4 in serum free media for 30 minutes. The medium was then replaced with normal growth media containing the compounds 2, 3 and 4 throughout the experiment. Cells were monitored daily for up to 72 hours then fixed, stained and photographed. As shown in FIGS. 4, 5 and 6, this experiment revealed that for all 3 compounds, the cells tolerate the compounds 2, 3 and 4 at concentrations from 25 to 100 µg/ml. Rows marked C in each of FIGS. 4 and 5, and FIG. 6 illustrate the results of treatment of Vero cells, which were not infected with HSV 1, and treated with compounds 2, 3 and 4.
Spread of HSV 1 and Virus Plaque Formation.

The inhibitory effect of compounds 2 and 3 was monitored on Vero cells. Cells were pre-treated with different concentrations of compounds 2 and 3, subsequently treated with buffer or buffer containing HSV 1. After two days of infection, cells were fixed stained and photographed. To determine whether the compounds can inhibit HSV 1 viral spreading or plaque formation, a plaque assay was performed in liquid to determine spreading (Row A in FIGS. 4 and 5) as well as in agar to determine plaque number (Row B in FIGS. 4 and 5). A strong inhibitory effect was observed by compound 2 and 3, as shown in FIGS. 4 and 5 respectively. Both compounds effectively reduce HSV 1 spreading as well as plaque number in Vero cells in a dose dependent manner.

Compounds 2 and 3 had No Inhibitory Effect on Vaccinia Virus Plaque Formation.

Figure 7:
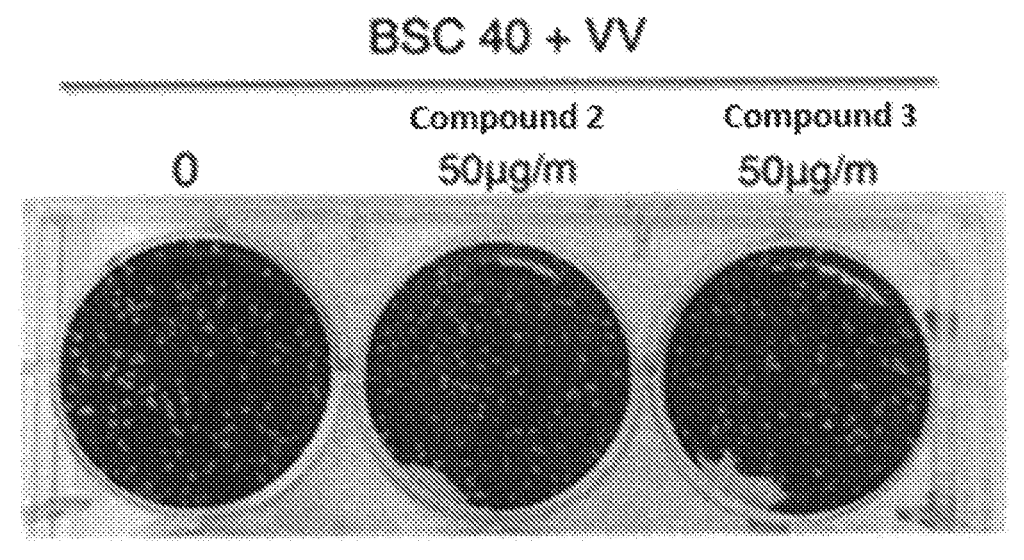

To test the specificity of compounds 2 and 3 on the HSV 1 virus, the compounds were also tested on the Vaccinia virus, which is a further DNA virus. BSC 40 cells were kept untreated or were pre-treated with the compounds at a concentration of 50 mg/ml and cells were then infected with Vaccinia virus and monitored side by side throughout the experiment. As shown in FIG. 7, none of compounds 2 or 3 inhibited Vaccinia virus (VV) plaque formation which indicates that the inhibitory effect of compounds 2 and 3 on HSV 1 infection is highly specific.

From the experiments mentioned above, it can be concluded that all cells tested can tolerate the compounds 2, 3 and 4 in concentrations from 0 to 100 μg/ml. Compound 2 and 3 both demonstrate a strong antiviral effect against HSV-1 infected Vero cells, both in terms of virus spreading and plaque formation. In the presence of 501 g/ml of the compounds, infectivity was reduced by 50%. In the presence of 100 μg/ml of the compounds, infectivity was reduced by 80%. None of the tested compounds are active towards the Vaccinia virus.

The invention claimed is:

1. A compound having the following formula:

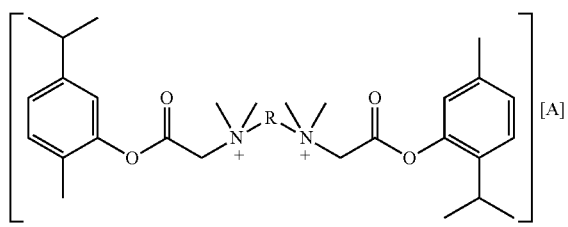

(I)

wherein R is an alkane chain having between 8 and 20 carbon atoms, and A is one or more anions having a total charge of −2;

or R is a quaternary amine having the following formula:

(Ia)

wherein $R_a$ and $R_b$ are each an alkane chain having between 8 and 20 carbon atoms, and A is one or more anions having a total charge of −3.

2. A compound according to claim 1, wherein R is a saturated linear alkane chain having between 8 and 16 carbon atoms.

3. A compound according to claim 1, wherein $R_a$ and $R_b$ are saturated linear alkane chains having between 8 and 16 carbon atoms.

4. A compound according to claim 1, wherein the one or more anions are selected from chloride anions and bromide anions.

5. A compound according to claim 1, having the following formula:

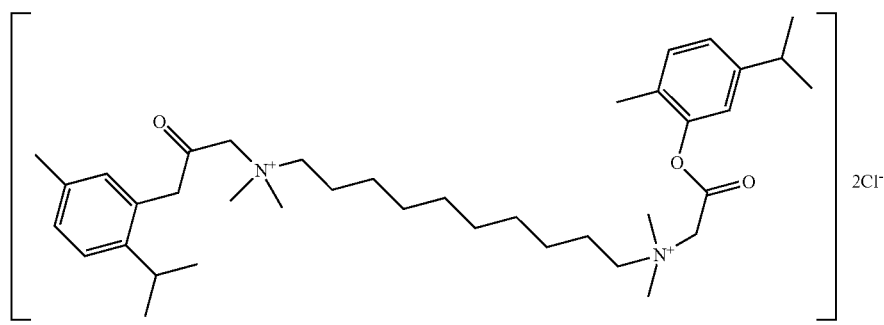

(II)

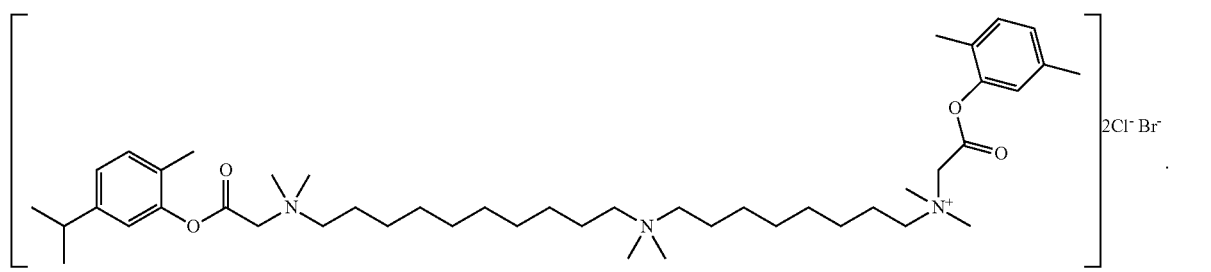

(III)

6. A compound having the following formula:

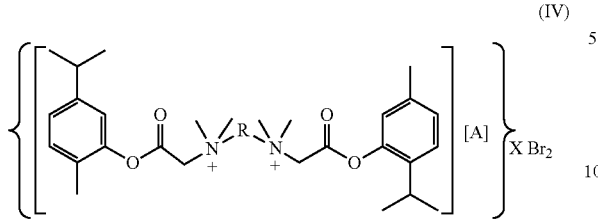

wherein R is an alkane chain having between 8 and 20 carbon atoms and A is one or more anions having a total charge of −2; or R is a quaternary amine having the following formula:

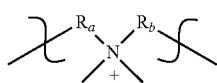

wherein $R_a$ and $R_b$ are each an alkane chain having between 8 and 20 carbon atoms, and A is one or more anions having a total charge of −3; and wherein X is 2, 4, 6, 8 or 10.

7. A compound according to claim 6, wherein R is a saturated linear alkane chain having between 8 and 16 carbon atoms.

8. A compound according to claim 6, wherein $R_a$ and $R_b$ are saturated linear alkane chains having between 8 and 16 carbon atoms.

9. A compound according to claim 6, wherein the one or more anions are selected from chloride anions and bromide anions.

10. A compound according to claim 6, having the following formula:

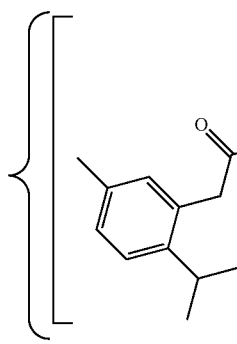

11. A pharmaceutical composition comprising:
the compound of claim 1 or claim 6; and a pharmaceutically acceptable carrier.

12. A method of treatment of Herpes virus, Human Papilloma virus, fungal infections and/or bacterial infections, comprising a step of administering to a subject a compound according to claim 1 or claim 6.

13. A process for producing the compound of claim 1, comprising:
i) reacting carvacrol with $R_2CH_2COCl$ to form a compound having the formula:

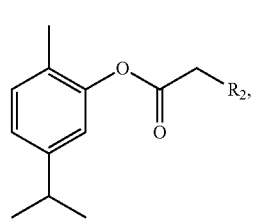

wherein $R_2$ is a halogen;

ii) reacting a compound having the formula

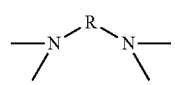

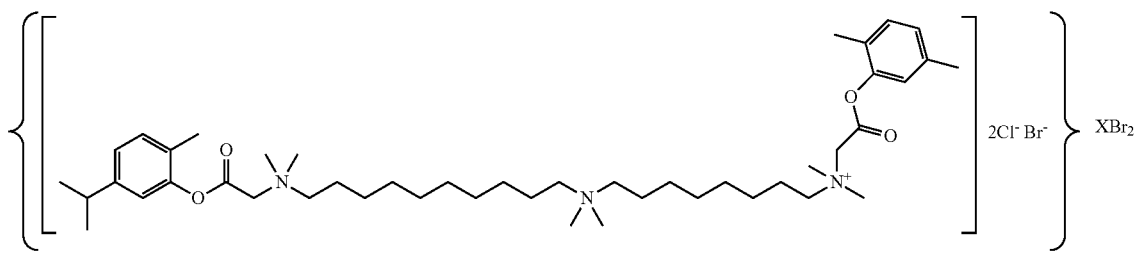

wherein X is 4, 8 or 10.

with the compound having the formula

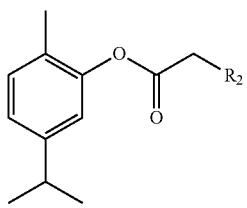
(VII)

to form the compound having the formula

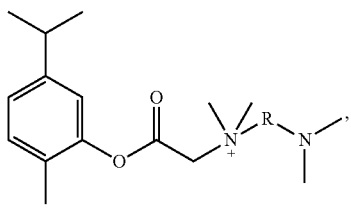
(IX)

wherein R is an alkane chain having between 8 and 20 carbon atoms; or
R is a quaternary amine having the following formula:

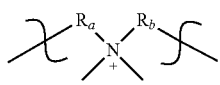
(Ia)

wherein $R_a$ and $R_b$ are each an alkane chain having between 8 and 20 carbon atoms;

iii) reacting thymol with $R_2CH_2COCl$ to form a compound having the formula

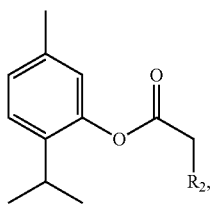
(X)

wherein $R_2$ is a halogen;
iv) reacting the compound having formula

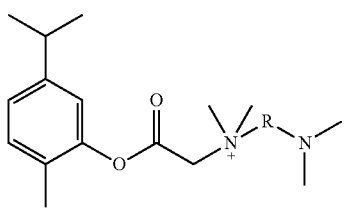
(IX)

with the compound having the formula

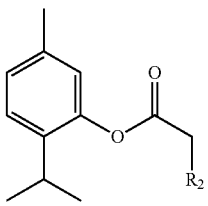
(X)

to form the final product having the formula

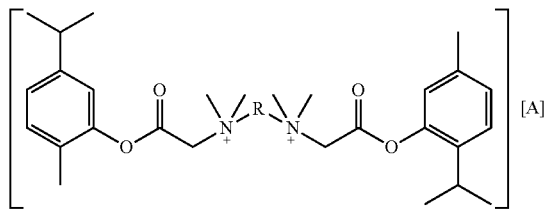
(I)

wherein R is an alkane chain having between 8 and 20 carbon atoms, and A is one or more anions having a total charge of −2; or R is a quaternary amine having the following formula:

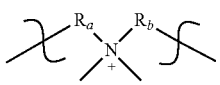
(Ia)

wherein $R_a$ and $R_b$ are each an alkane chain having between 8 and 20 carbon atoms, and A is one or more anions having a total charge of −3.

14. A process according to claim 13, wherein R is a saturated linear alkane chain having between 8 and 16 carbon atoms.

15. A process according to claim 13, wherein $R_a$ and $R_b$ are each a saturated linear alkane chain having between 8 and 16 carbon atoms.

16. A process according to claim 13, further comprising one or more steps of separation and/or extraction.

17. A process for the production of a compound according to claim 6, comprising reacting the compound having the formula

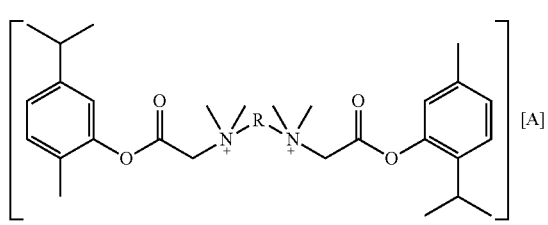
(II)

with bromine to form a compound having the formula

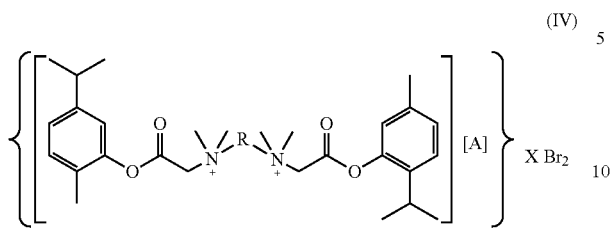

wherein R is an alkane chain having between 8 and 20 carbon atoms and A is one or more anions having a total charge of −2; or R is a quaternary amine having the following formula:

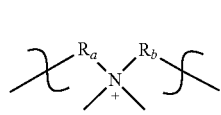

wherein $R_a$ and $R_b$ are each an alkane chain having between 8 and 20 carbon atoms, and A is one or more anions having a total charge of −3; and wherein X is 2, 4, 6, 8 or 10.

18. A compound having the following formula:

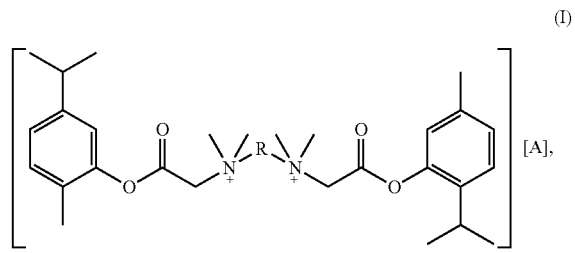

wherein R is an alkane chain having between 8 and 20 carbon atoms and A is one or more anions having a total charge of −2; or R is a quaternary amine having the following formula:

wherein $R_a$ and $R_b$ are each an alkane chain having between 8 and 20 carbon atoms, and A is one or more anions having a total charge of −3; and wherein the compound is complexed with bromine.

* * * * *

UNITED STATES PATENT AND TRADEMARK OFFICE
CERTIFICATE OF CORRECTION

PATENT NO. : 10,858,308 B2
APPLICATION NO. : 16/476977
DATED : December 8, 2020
INVENTOR(S) : Gaik Babikyan et al.

It is certified that error appears in the above-identified patent and that said Letters Patent is hereby corrected as shown below:

On the Title Page

Item (57), Column 2, Line 5 of Abstract, "Ra and Rb" should be --$R_a$ and $R_b$--.

In the Specification

Column 1, Line 3, text is missing. It should be --FIELD OF THE INVENTION--.

Column 1, Line 5 (before "BACKGROUND"), text is missing. It should be --The present invention relates to compounds that may be used to treat Herpesviradae, Human Papilloma Virus, bacterial infections and fungal infections.--.

Column 1, Line 64, "infection" should be --infections--.

Column 3, Line 56, "$R_a$ and $R_b$ is" should be --$R_a$ and $R_b$ are--.

Column 5, Line 19, "R and $R_b$ are" should be --$R_a$ and $R_b$ are--.

Column 6, Line 15, "$R_a$ and $R_b$ is" should be --$R_a$ and $R_b$ are--.

Column 6, Formula VI, "2Cl•$Br^+$" should be --2$Cl^-$ $Br^-$--.

Column 7, Line 8, "formula" should be --formulas--.

Column 7, Line 25, "formula" should be --formulas--.

Column 7, Line 29, "formula" should be --formulas--.

Column 7, Line 50, "such as aqueous solution, non toxic" should be --such as an aqueous solution, nontoxic--.

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,858,308 B2

Column 8, Line 1, "includes," should be --include,--.

Column 11, Line 55, "n wherein n is the number" should be --wherein n is the number--.

Column 12, Line 3, "$R_a$ and $R_b$ is" should be --$R_a$ and $R_b$ are--.

Column 12, Line 29, "Rc" should be --$R_c$--.

Column 12, Line 58, "Rc" should be --$R_c$--.

Column 16, Line 39, "2.87 (q, 1H, -CH), 3.04 (q, 1H, -CH), 3.47 (s, 2H," should be --2.87 (q, 1H, -CH), 3.04 (q, 1H, -CH), 3.47 (s, 12H,--.

Column 16, Line 47, "(2-oxoethyldimethyl)azaniumyl" should be --(2-oxoethyl)(dimethyl)azaniumyl--.

Column 18, Line 31, "suspension" should be --suspensions--.

Column 18, Line 42, "pipette" should be --pipette.--.

Column 19, Line approx. 21, "non bold numbers" should be --nonbold numbers--.

Column 20, Line 61, "cells were fixed stained and" should be --cells were fixed, stained and--.

Column 20, Line 67, "compound 2 and 3," should be --compounds 2 and 3,--.

Column 21, Lines 17-18, "Compound 2 and 3" should be --Compounds 2 and 3--.

In the Claims

Column 22, Claim 5, in formulas (II) and (III), text is missing. There is an "O" missing from the left side of formula (II), and the word "or" is missing between the two formulas. In formula (III), there are also two lines missing at the left of the ring structure that is shown at the right-hand side of the formula.

Column 23, Claim 10, in formulas (V) and (VI), text is missing. There is an "O" missing from the left side of formula (V), and the word "or" is missing between the two formulas. In formula (VI), there are also two lines missing at the left of the ring structure that is shown at the right-hand side of the formula.